United States Patent
Al-Khattaf et al.

(10) Patent No.: US 8,697,593 B2
(45) Date of Patent: Apr. 15, 2014

(54) ZEOLITE CATALYST FOR THE ALKYLATION OF TOLUENE WITH METHANOL

(75) Inventors: Sulaiman S. Al-Khattaf, Dhahran (SA); Hideshi Hattori, Sapporo (JP); Balkrishna B. Tope, Dhahran (SA); Abdullah M. Aitani, Dhahran (SA)

(73) Assignees: King Fahd University of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 107 days.

(21) Appl. No.: 13/418,202

(22) Filed: Mar. 12, 2012

(65) Prior Publication Data

US 2013/0237735 A1     Sep. 12, 2013

(51) Int. Cl.
*B01J 29/06*     (2006.01)

(52) U.S. Cl.
USPC ............. 502/73; 502/60; 502/65; 502/66; 502/74; 502/75; 502/79

(58) Field of Classification Search
USPC ............ 502/60, 65, 66, 73, 74, 75, 79
See application file for complete search history.

(56) References Cited

U.S. PATENT DOCUMENTS

| | | | |
|---|---|---|---|
| 4,115,424 A | 9/1978 | Unland et al. | |
| 4,140,726 A | 2/1979 | Unland et al. | |
| 4,429,174 A | 1/1984 | Teng et al. | |
| 4,463,204 A * | 7/1984 | Liu | 585/437 |
| 4,483,936 A | 11/1984 | Liu et al. | |
| 4,483,937 A * | 11/1984 | Liu | 502/73 |
| 4,613,720 A | 9/1986 | Bonifaz et al. | |
| 4,752,596 A * | 6/1988 | Bergna et al. | 502/64 |
| 5,068,483 A | 11/1991 | Barthomeuf et al. | |
| 6,114,268 A * | 9/2000 | Wu et al. | 502/74 |
| 7,011,811 B2 | 3/2006 | Elomari | |
| 7,919,661 B2 | 4/2011 | Pelati et al. | |

FOREIGN PATENT DOCUMENTS

| | | |
|---|---|---|
| DE | 33 30 790 A1 | 3/1985 |
| JP | 57-68144 | 4/1982 |

* cited by examiner

*Primary Examiner* — Elizabeth Wood

(74) *Attorney, Agent, or Firm* — Richard C Litman

(57) ABSTRACT

The zeolite catalyst is provided for the alkylation of toluene with methanol to selectively produce styrene and ethylbenzene. The zeolite catalyst is an X-type zeolite modified sequentially, first by ion-exchange with alkali metals, such as cesium, to replace all exchangeable sodium from the zeolite, and then by mixing the modified zeolite with borate salts of a metal such as lanthanum, zirconium, copper, zinc or the like. The initial zeolite composition has a Si to Al molar ratio of approximately 1 to 10, and is preferably either zeolite X or zeolite 13X. The zeolite composition is ion-exchanged with cesium to replace at least 50% of the exchangeable sodium in the zeolite composition. The ion-exchanged zeolite composition is then mixed with a borate salt to form the zeolite catalyst for the alkylation of toluene with methanol for the selective production of styrene and ethylbenzene.

2 Claims, No Drawings

ZEOLITE CATALYST FOR THE ALKYLATION OF TOLUENE WITH METHANOL

BACKGROUND OF THE INVENTION

1. Field of the Invention

The present invention relates the production of styrene, and particularly to a zeolite catalyst for the alkylation of toluene with methanol to selectively produce styrene and ethylbenzene.

2. Description of the Related Art

Styrene is a commercially valuable commodity typically produced using benzene and ethylene feeds in a two-step process. The first step is the alkylation of the benzene with ethylene to produce ethylbenzene. In the second step, ethylbenzene is dehydrogenated to form styrene. This reaction occurs at high temperatures (greater than 600° C.) using an iron oxide catalyst. The reaction is highly endothermic and thermodynamically limited.

The production of styrene from ethylbenzene consumes ten times more energy than the production of most other chemicals, and is also a major contributor to the production of harmful greenhouse gases, such as methane gas emissions. The current global production capacity of styrene is near 26 million tons per year and is increasing at a steady rate (~3.7% per year). Styrene is used as an intermediate chemical in the production of various polymers, mainly polystyrene.

There is a need for an alternative technique for the producing styrene that is relatively energy efficient and that reduces greenhouse gas emissions. Thus, a zeolite catalyst for the alkylation of toluene with methanol solving the aforementioned problems is desired.

SUMMARY OF THE INVENTION

The zeolite catalyst for the alkylation of toluene with methanol provides a catalyst and a process for producing styrene that is energy efficient and reduces greenhouse gas emissions compared to conventional methods. The zeolite catalyst is an X-type zeolite modified sequentially, first by ion-exchange with alkali metals, such as cesium, to replace all exchangeable sodium from the zeolite, and then by mixing with borate salts of metals such as lanthanum, zirconium, copper, zinc or the like.

The initial zeolite composition has a Si to Al (silicon to aluminum, as opposed to silica to alumina) molar ratio of 1 to 10, and is preferably either zeolite X or zeolite 13X having a surface area density of between approximately 400 $m^2/g$ and approximately 600 $m^2/g$. The zeolite composition is ion-exchanged with cesium to replace at least 50% of the exchangeable sodium in the zeolite composition. The ion-exchanged zeolite composition is then mixed with a borate salt of lanthanum, zirconium, and divalent and trivalent cations of Mg, Cr, Fe, Zn, Mn, Co, Ni, Cu, Cd, Sn, Al, Ga, In, Fe, V, Cr, Ti, Pb, Mn, Co, Rh, Ni, Si or mixtures thereof. The mixture forms the zeolite catalyst for the alkylation of toluene with methanol for the selective production of styrene and ethylbenzene.

These and other features of the present invention will become readily apparent upon further review of the following specification.

DETAILED DESCRIPTION OF THE PREFERRED EMBODIMENTS

The present invention relates to a zeolite catalyst for the alkylation of toluene with methanol to selectively produce styrene and ethylbenzene. The zeolite catalyst is an X-type zeolite that is modified sequentially, first by ion-exchange with alkali metals, such as cesium, to replace all exchangeable sodium from the zeolite, and then by mixing with borate salts of metals, such as lanthanum, zirconium, copper, zinc or the like. As used herein, an X-type zeolite (or zeolite X) is a synthetic faujasite zeolite having a silica to alumina molar ratio of about 2 to 3 (a silicon to aluminum molar ratio of about 1 to 1.5). In general, the zeolite catalyst acts as an alkylating agent that alkylates an aromatic compound to produce a C8 aromatic product, particularly styrene and ethylbenzene, with styrene being prominently and selectively formed.

The initial zeolite composition has a Si to Al molar ratio of approximately 1 to 10, and is preferably either zeolite X or zeolite 13X having a surface area density of between approximately 400 $m^2/g$ and approximately 600 $m^2/g$. In the zeolite X or zeolite 13X, the charge of the acidic zeolite (containing aluminum) is balanced by the sodium cations, which are typically present in amounts sufficient to neutralize the negative charge.

The zeolite composition is ion-exchanged with cesium to replace at least 50% of the exchangeable sodium in the zeolite composition. The ion-exchanged zeolite composition is then mixed with a borate salt of lanthanum, zirconium, and divalent and trivalent cations of Mg, Cr, Fe, Zn, Mn, Co, Ni, Cu, Cd, Sn, Al, Ga, In, Fe, V, Cr, Ti, Pb, Mn, Co, Rh, Ni, Si or mixtures thereof. The mixture forms the zeolite catalyst for the alkylation of toluene with methanol for the selective production of styrene and ethylbenzene.

In order to form the styrene product, the zeolite catalyst is contacted with a feed gas mixture of toluene and methanol. Preferably, the toluene and the methanol have a molar ratio of between about 4 to 1 and about 8 to 1. The reaction preferably occurs at a temperature of between 300° C. and 550° C. An inert diluent gas may be added to the feed gas mixture. The inert diluent gas may be nitrogen gas, which is provided such that the feed gas mixture has a molar ratio of the toluene and methanol mixture to the nitrogen gas of between about 1 to 1 and about 6 to 1. Alternatively, the feed gas mixture may have a molar ratio of the toluene to the nitrogen gas of between about 0.5 to 1 and about 6 to 1. As a further alternative, the feed gas mixture may have a molar ratio of the methanol to the nitrogen gas of between about 0.2 to 1 and about 6 to 1.

In the following, the percentage of methanol conversion is calculated as [(methanol wt % in the feed gas)−(methanol wt % in the product)×100]/(methanol wt % in the feed gas). Similarly, the percentage of toluene conversion is calculated as [(toluene wt % in the feed gas)−(toluene wt % in the product)×100]/(toluene wt % in the feed gas).

EXAMPLE 1

In the first example, a cesium-modified zeolite-13X (Cs13X) composition of the sodium form was prepared by a multiple sequential ion exchange and centrifuging. NaX (sodium form of zeolite X) obtained from Junsei Chemicals was ion-exchanged with Cs+ ions. The NaX had a Si/Al ratio of 1.24 and a surface area of 527 $m^2/g$. 30 g of the NaX was immersed in 200 ml of an aqueous solution of cesium hydroxide (0.35 M), which was then stirred for eight hours. The slurry was then centrifuged at 3,000 RPM.

The top layer of solution was removed and the remaining solid cake was again immersed in 200 ml of an aqueous solution of cesium hydroxide (0.35 M) and stirred for another eight hours. The immersion and centrifuge procedures were conducted five times in order to ensure that a maximum amount of the sodium was exchanged with cesium. The resulting slurry was filtered, washed with distilled water, and then dried in an oven at 120° C. The dried sample was calcined at 480° C. for four hours.

EXAMPLE 2

In the second example, the Cs13X with 10 wt % of lanthanum borate (LaBorate) was prepared. In Table 1 below, this second example is shown as Catalyst A. 3 g of a boron trioxide solid sample (ground to a fine powder) was mixed with 3 g of lanthanum oxide (a weight ratio of 1:1), and was then homogenized with an agate mortar and pestle. The mixture was then placed in a platinum crucible and kept in a resistance-heating muffle furnace. Argon gas with a flow rate of 40 ml/min passed through the furnace during the reaction. The furnace was heated to 1100° C. with a ramp rate of 10° C./min, held for three hours, and then allowed to cool to room temperature. A white powder was obtained after the reaction, providing LaBorate.

The Cs13X-10 wt % LaBorate was synthesized from cesium-modified zeolite-X (prepared as in Example 1) and the synthesized LaBorate as follows: 0.10 g of lanthanum borate (prepared by the above procedure) was mixed with 0.90 g of Cs13X zeolite. The mixture was mechanically ground with a mortar for 30 minutes, and then dried and calcined with a slow ramp rate of 2° C./min at 500° C. for three hours. The resulting powder was pelletized, crushed, and sieved to a particle size between 0.5 mm to 1.0 mm and used for the side chain alkylation reaction. The resultant catalyst has 10 wt % lanthanum borate loaded over cesium-modified zeolite-X.

EXAMPLE 3

In the third example, Cs13X-10 wt % ZrBorate (Catalyst B) was prepared. Zirconium borate (ZrBorate) was first prepared as follows: 19.10 g of disodium tetraborate was dissolved in 150 ml of water by ultrasonication. The solution was continuously stirred at room temperature. Another solution was prepared by dissolving 8.2 g of zirconium nitrate in water, and the zirconium nitrate solution was added slowly to the solution of disodium tetraborate, under continuous stirring. The resulting precipitate was filtered, thoroughly washed and dried in an oven at 120° C., and then calcined at 450° C. for four hours, forming the ZrBorate.

The Cs13X-10 wt % ZrBorate (Catalyst B) was synthesized from cesium-modified zeolite-X and the above synthesized ZrBorate as follows: 0.10 g of the zirconium borate was mixed with 0.90 g of Cs13X zeolite. The mixture was mechanically ground with a mortar for 30 minutes, then dried and calcined with a slow ramp rate of 2° C./min at 500° C. for three hours. The resulting powder was pelletized, crushed, and sieved to a particle size between 0.5 mm to 1.0 mm and used for the side chain alkylation reaction.

EXAMPLE 4

In the fourth example, Cs13X-10 wt % CuBorate (Catalyst C) was prepared. First, the copper borate (CuBorate) was prepared as follows: 19.10 g of disodium tetraborate was dissolved in 150 ml of water by ultrasonication. The solution was continuously stirred at room temperature. Another solution was prepared by dissolving 8.20 g of copper nitrate in water, and the copper nitrate solution was added slowly to the solution of disodium tetraborate under continuous stirring.

The resulting precipitate was filtered, thoroughly washed and dried in an oven at 120° C., and then calcined at 450° C. for four hours to produce the CuBorate.

The Cs13X-10 wt % CuBorate was synthesized from cesium-modified zeolite X and the CuBorate as follows: 0.10 g of the copper borate was mixed with 0.90 g of Cs13X zeolite. The mixture was mechanically ground with a mortar for 30 minutes, then dried and calcined with a slow ramp rate of 2° C./min at 500° C. for three hours. The resulting powder was pelletized, crushed, and sieved to a particle size between 0.5 mm to 1.0 mm and used for the side chain alkylation reaction.

EXAMPLE 5

In the fifth example, Cs13X-10 wt % ZnBorate (Catalyst D) was prepared. The zinc borate loaded cesium-modified zeolite X (Cs13X-10 wt % ZnBorate) was synthesized from cesium-modified zeolite X and zinc borate (ZnBorate) as follows: 0.10 g of zinc borate was mixed with 0.90 g of Cs13X zeolites. The reaction occurred for six hours, and the resultant was dried and calcined with a slow ramp rate of 2° C./min at 500° C. for three hours. The resulting powder was pelletized, crushed and sieved to a particle size between 0.5 mm to 1.0 mm and used for the side chain alkylation reaction.

The catalysts of Examples 1-5 above were tested for their activity and selectivity to side chain alkylation reactions in a fixed bed continuous flow reactor at atmospheric pressure. A fixed amount of catalyst sample (400 mg) was packed in the reactor tube with alumina balls on the top and bottom of the reactor. The alumina balls at the top provided the preheating zone to the catalyst bed. The reactor was checked for leaks and then pretreated under $N_2$ at a flow rate of 40 ml/min. Temperature was increased from room temperature to 450° C. at 10° C./min and kept at this temperature for one hour. Then, the temperature was decreased to 410° C., and the feed was started at a rate of 0.12 ml/min. The feed was a mixture of toluene and methanol in a ratio of 6 moles of toluene to 1 mole of methanol.

The feed rate and nitrogen flow were kept constant throughout the experiments, and the nitrogen/feed ratio was 1.43. After 1.5 hours of continuous feed flow, the online injection was made and the reaction products were analyzed using an online gas chromatograph. Three consecutive online injections were made in order to provide representative and reliable reaction product sampling and analysis. In practice, any unreacted feed may be stripped from the products and the styrene may be separated from the ethylbenzene using conventional processes to collect the desired styrene product.

Table 1 below presents the results of the catalyst evaluation, comparing conversion and selectivity of the five catalysts (Cs13X, Catalyst A, Catalyst B, Catalyst C, and Catalyst D) using a feed composition of toluene and methanol in a molar ratio of 6:1 at a liquid hour space velocity of 12 $h^{-1}$, a nitrogen/feed ratio of 3.0, and at a reaction temperature of 410° C. Catalysts A and B were further tested for two more reaction temperatures (450° C. and 500° C.) and two more liquid hour space velocities of 8 $h^{-1}$ and 20 $h^{-1}$. The results are also presented in Table 1 below.

TABLE 1

Catalyst Testing

| Catalyst | Reaction Temp. (°C.) | LHSV, h$^{-1}$ | MeOH Conv. % | Toluene Conv. % | Styrene/ (Styrene + EB) % | Styrene + EB Selectivity % |
|---|---|---|---|---|---|---|
| Cs13X | 410 | 12 | 28.7 | 1.7 | 85.3 | 80.8 |
| A | 410 | 12 | 43.4 | 1.9 | 92.2 | 98.4 |
|   | 410 | 8 | 55.0 | 2.9 | 87.8 | 96.07 |
|   | 410 | 20 | 22.2 | 1.76 | 93.6 | 80.98 |
|   | 450 | 12 | 67.7 | 3.4 | 79.1 | 98.9 |
|   | 500 | 12 | 80.2 | 3.9 | 60.3 | 80.2 |
| B | 410 | 12 | 42.5 | 1.6 | 93.2 | 95.5 |
|   | 410 | 8 | 46.5 | 1.9 | 89.3 | 98.4 |
|   | 410 | 20 | 37.3 | 1.3 | 95.3 | 94.8 |
|   | 450 | 12 | 51.3 | 2.9 | 82.8 | 97.9 |
|   | 500 | 12 | 88.9 | 5.8 | 62.9 | 98.6 |
| C | 410 | 12 | 44.9 | 2.4 | 93.9 | 93.6 |
| D | 410 | 12 | 44.7 | 4.6 | 95.0 | 92.5 |

The side-chain alkylation of toluene with methanol to produce styrene selectively is efficient and economical, compared to the conventional process. Additionally, the production method operates at a relatively low reaction temperature of 400 to 450° C. and at atmospheric pressure. Thus, this process has lower greenhouse gas emissions compared to conventional techniques, and further reduces feedstock costs by 35%.

It is to be understood that the present invention is not limited to the embodiments described above, but encompasses any and all embodiments within the scope of the following claims.

We claim:

1. A zeolite catalyst for the alkylation of toluene with methanol to produce styrene, comprising a mixture of:
    a zeolite composition having a Si-to-Al molar ratio of about 1 to 10, the zeolite composition being ion-exchanged with cesium to replace sodium cations in the zeolite composition, said zeolite composition comprising zeolite X; and
    a borate salt of at least one metal selected from the group consisting of lanthanum and zirconium.

2. The zeolite catalyst as recited in claim 1, wherein at least 50% of the sodium in the zeolite composition is ion-exchanged with the cesium.

* * * * *